United States Patent [19]

Yu

[11] 4,159,274

[45] Jun. 26, 1979

[54] 7-NITRO-2-BENZOFURANCARBOXIMIDA-MIDE HYDROCHLORIDE

[75] Inventor: Chia-Nien Yu, Norwich, N.Y.

[73] Assignee: Morton-Norwich Products, Inc., Norwich, N.Y.

[21] Appl. No.: 932,474

[22] Filed: Aug. 10, 1978

Related U.S. Application Data

[63] Continuation-in-part of Ser. No. 886,646, Mar. 15, 1978, abandoned.

[51] Int. Cl.² ........................................... C07D 307/85
[52] U.S. Cl. .................................................. 260/346.73
[58] Field of Search ..................................... 260/346.73

[56] References Cited

U.S. PATENT DOCUMENTS 3,906,010  9/1975  Pelosi, Jr. et al. ................. 260/347.5

OTHER PUBLICATIONS

Areschka et al., Chem. Abstr., vol. 85, 46281 (1976).

*Primary Examiner*—Natalie Trousof
*Assistant Examiner*—Bernard Dentz
*Attorney, Agent, or Firm*—Anthony J. Franze

[57] ABSTRACT

7-Nitro-2-Benzofurancarboximidamide Hydrochloride is useful as an antidepressant.

1 Claim, No Drawings

7-NITRO-2-BENZOFURANCARBOXIMIDAMIDE HYDROCHLORIDE

This application is a continuation-in-part of my copending application Ser. No. 886,646 filed Mar. 15, 1978, now abandoned.

This invention is concerned with the chemical compound 7-nitro-2-benzofurancarboximidamide. It possesses pharmacological activity affecting the central nervous system. When administered perorally to animals, it exhibits an antidepressant effect. Such effect is evidenced in the control of tetrabenazine induced ptosis in mice. Thus, an oral dose of 50 mg/kg to mice receiving intraperitoneally 35 mg/kg of tetrabenazine counteracts the ptosis producing propensity of tetrabenazine.

The compound of this invention can be combined with various adjuvants and excipients commonly employed in the pharmaceutical art to provide various pharmaceutical dosage forms such as tablets, suspensions, solutions, capsules, elixirs, and the like.

The method which is currently used for the preparation of the compound of this invention is illustrated by the following description.

A. PREPARATION OF COUMARILALDEHYDE

A solution of benzofuran (163 g, 1.39 mole) in dimethylformamide (264 g, dried over magnesium sulfate overnight) in a 2-l, 3-necked flask was stirred and treated dropwise with phosphorus oxychloride (233 g, 136 ml). The solution was heated and stirred on a steam bath for 8 hrs. Another 88 g of dry dimethylformamide, followed by 70 g (42 ml) of phosphorus oxychloride, was added and the heating and stirring were continued overnight. After cooling, the solution was slowly poured into a stirred solution of 260 g of sodium acetate in 1500 ml of water. The solution was extracted four times with 500 ml of ether. The ether extracts were washed with dilute aqueous sodium hydroxide solution and then with water. The solution was then dried over magnesium sulfate and filtered.

The ether was evaporated and the residue was distilled at reduced pressure to give 13 g of benzofuran in the forerun. The product, a yellow liquid that turned dark on standing, was collected at 67°–70° at 0.1 mm in a yield of 99 g (54%).

B. PREPARATION OF 7-NITROCOUMARILALDEHYDE DIACETATE

Coumarilaldehyde (88 g, 0.6 mole) was dissolved in acetic anhydride (400 ml) with cooling and six drops of concentrated sulfuric acid were added dropwise with ice bath cooling and stirring. The stirred solution was treated dropwise with concentrated nitric acid (50 ml) at 0°–5° and then allowed to warm to room temperature with stirring. A yellow solid precipitated. The mixture was cooled in an ice bath for ½ hour with continued stirring. The solid was filtered, washed with a 1:1 solution of ether and hexane, and air dried on the funnel to yield 70 g (39%), m.p. 129°–130°. Several recrystallizations of a sample from isopropanol (20 ml/g, Darco) gave tan needles, m.p. 130°–132°.

Anal. Calcd. for $C_{13}H_{11}NO_7$: C, 53.24; H, 3.78; N, 4.78. Found: C, 53.42,53.34; H, 3.88,3.83; N, 4.80,4.74.

C. PREPARATION OF 7-NITROCOUMARILALDEHYDE

B. (73 g, 0.25 mole) was added in portions to concentrated sulfuric acid (365 ml) with stirring and cooling to keep the temperature below 30°. The resulting green solution was stirred at room temperature for 20 min. and poured over ice to give a tan solid. The solid was collected by filtration, washed with water and dried at 60° to yield 45 g (95%), m.p. 100°–130°. Recrystallization from benzene (20 ml/g, Darco) gave 32 g of light tan needles, m.p. 180°–181°. Several recrystallizations of sample from benzene (30 ml/g) raised the melting point to 181°–182° (corr).

Anal. Calc'd. for $C_9H_5NO_4$: C, 56.55; H, 2.64; N, 7.33. Found: C, 56.58,56.56; H, 2.56,2.57; N, 7.18,7.21.

D. PREPARATION OF 7-NITROCOUMARILALDEHYDE OXIME

A mixture of 7-nitrocoumarilaldehyde (24.8 g, 0.13 mole), hydroxylamine hydrochloride (9 g., 0.13 mole), and 2-methoxyethanol (250 ml.) was heated to boiling to give a yellow solution. Heating was continued on a steam bath for 1 hr. The warm solution was diluted with water (500 ml.) to give a cream colored solid. After cooling in an ice bath, the solid was collected by filtration, washed with water and dried at 100° to yield 25 g. (93%), m.p. 180°–184°. Recrystallization from isopropanol (10 ml./g., Darco) and drying at 100° gave 20 g. of cream colored needles; m.p. 182°–184°. Several recrystallizations of a sample from isopropanol increased the melting point to 182.5°–184° (corr.).

Anal. Calc'd. for $C_9H_6N_2O_4$: C, 52.43; H, 2.93; N, 13.59. Found: C, 52.18,52.24; H, 2.76,2.80; N, 13.21,13.35.

E. 7-NITRO-2-BENZOFURANCARBOXIMIDAMIDE HYDROCHLORIDE

A mixture of 8.9 g (0.043 mole) of D. in 100 ml of acetic anhydride and 2 g of anhydrous sodium acetate was heated to reflux for 5½ hrs. After cooling, the dark solution was poured onto crushed ice. Grayish solid separated and was filtered, washed well with water and air-dried. The crude nitrile (5.3 g) was boiled in 800 ml of methylcyclohexane and a minimum amount of benzene. The mixture was filtered while still hot. Crystalline solid separated from the yellow solution. The solid was filtered, washed with hexane and air-dried to give 4.0 g of product. Concentration of the filtrate gave another 0.4 of the nitrile.

The nitrile (4.4 g) was placed in 360 ml of anhydrous MeOH and heated to boiling on a steam bath. Only about half of solid dissolved after 5 min. of boiling. Two small spatulas of sodium methoxide powder was added and a red solution resulted very readily. The solution was allowed to stir without heating and in about 10–15 minutes crystalline solid separated. The mixture was allowed to cool gradually with stirring. The solid was collected, washed with ether and air-dried. The yield of the imidate was 2.8 g. A second crop of 2.0 g was obtained from the filtrate.

The combined imidate (4.8 g) was placed in 350 ml of anhydrous MeOH and warmed on a steam bath until a clear solution resulted (5–10 min.). After slight cooling, 1.17 g of anhydrous ammonium chloride was added with stirring. The solid $NH_4Cl$ dissolved in about 5 min. and 10–15 min. later, yellow solid started to separate. After being stirred overnight at ambient temperature, the mixture was heated at reflux for 2 hrs. The reaction mixture was filtered and the filtrate was concentrated at reduced pressure to give a yellow solid residue. The solid was triturated with water and filtered. The water insoluble material was shown by infrared spectrum to be starting imidate. The recovered imidate was further heated with ammonium chloride in anhydrous MeOH. The reaction mixture was worked up as before. The combined aqueous filtrate was made alkaline with conc. NH$_4$OH and jelly like solid separated. The solid was collected, washed well with water and dried. The free amidine was then pulverized and triturated with an ethanolic HCl solution. The color of the solid changed from light brown to white. The solid was collected, washed well with ether and air-dried to give 2.1 g (20% overall yield).

Anal. Calc'd. for C$_9$H$_7$N$_3$O$_3$.HCl: C, 44.73%; H, 3.34%; N, 17.39%. Found: C, 45.00%; H, 3.50%; N, 17.15%.

What is claimed is:
1. The compound 7-Nitro-2-benzofurancarboximidamide hydrochloride.